(12) United States Patent
Schneider et al.

(10) Patent No.: US 10,600,504 B2
(45) Date of Patent: Mar. 24, 2020

(54) SYSTEMS AND METHODS FOR SORTING FINDINGS TO MEDICAL CODERS

(71) Applicant: Apixio, Inc., San Mateo, CA (US)

(72) Inventors: John O. Schneider, Los Gatos, CA (US); Vishnuvyas Sethumadhavan, Mountain View, CA (US); Robert Derward Rogers, Pleasanton, CA (US)

(73) Assignee: APIXIO, INC., San Mateo, CA (US)

( * ) Notice: Subject to any disclaimer, the term of this patent is extended or adjusted under 35 U.S.C. 154(b) by 0 days.

(21) Appl. No.: 14/498,594

(22) Filed: Sep. 26, 2014

(65) Prior Publication Data

US 2015/0095065 A1 Apr. 2, 2015

Related U.S. Application Data

(60) Provisional application No. 61/883,967, filed on Sep. 27, 2013.

(51) Int. Cl.
*G16H 10/60* (2018.01)
*G06F 19/00* (2018.01)
*G16H 15/00* (2018.01)

(52) U.S. Cl.
CPC ............ *G16H 10/60* (2018.01); *G06F 19/00* (2013.01); *G06F 19/328* (2013.01); *G16H 15/00* (2018.01)

(58) Field of Classification Search
CPC .. G06F 19/322; G06F 19/3487; G06F 19/328; G06F 19/00; G16H 50/70; G16H 15/00; G16H 10/60; G16H 40/20; G06Q 50/24

USPC .... 705/3, 2, 1.1, 7.13–7.17, 7.38–7.42, 320, 705/321
See application file for complete search history.

(56) References Cited

U.S. PATENT DOCUMENTS

| | | | |
|---|---|---|---|
| 7,321,861 B1 | 1/2008 | Oon | |
| 2001/0042080 A1* | 11/2001 | Ross | G06F 19/328 715/225 |
| 2002/0010679 A1 | 1/2002 | Felsher | |
| 2003/0229510 A1* | 12/2003 | Kerr | G06Q 10/10 705/321 |
| 2004/0249667 A1 | 12/2004 | Oon | |

(Continued)

OTHER PUBLICATIONS

USPTO, ISA/US, "Notification of Transmittal of the ISR and the Written Opinion of the International Searching Authority, or the Declaration," in PCT Application No. PCT/US2014/057929, dated Jan. 27, 2015, 8 pages.

*Primary Examiner* — Igor N Borissov
(74) *Attorney, Agent, or Firm* — Kang S. Lim (57) ABSTRACT

A sorter of medical findings for assessment by a medical coder is provided. In some embodiments, the sorter receives information about a user (coder), including identification, a role, and historical activity. The sorter determines whether to run in exploration or exploitation modes. Exploration is used to explore the scope of the findings and also identify variables that impact a finding. Exploitation is designed to maximize a goal (such as throughput or profitability). Lastly a finding is selected and provided to the user. The selection is based upon computing internal parameters when in exploration, or based upon optimizing for criteria when in exploitation. The sorter may also determine competency for the user, and cut them off from performing additional coding if they are found incompetent.

12 Claims, 9 Drawing Sheets

(56) References Cited

U.S. PATENT DOCUMENTS

| | | | |
|---|---|---|---|
| 2005/0043986 A1* | 2/2005 | McConnell | H04M 3/5232 379/265.02 |
| 2006/0036619 A1 | 2/2006 | Fuerst et al. | |
| 2006/0047669 A1 | 3/2006 | Durrence et al. | |
| 2006/0112050 A1 | 5/2006 | Miikkulainen et al. | |
| 2006/0129435 A1 | 6/2006 | Smitherman et al. | |
| 2007/0192143 A1* | 8/2007 | Krishnan | G06Q 10/10 705/3 |
| 2008/0077443 A1* | 3/2008 | Singer | G16H 10/60 705/3 |
| 2008/0091633 A1 | 4/2008 | Rappaport et al. | |
| 2008/0120296 A1 | 5/2008 | Kariathungal et al. | |
| 2008/0270340 A1 | 10/2008 | Abrams et al. | |
| 2009/0024615 A1 | 1/2009 | Pedro et al. | |
| 2009/0070103 A1 | 3/2009 | Beggelman et al. | |
| 2009/0112882 A1 | 4/2009 | Maresh et al. | |
| 2009/0136102 A1 | 5/2009 | Kimpe et al. | |
| 2009/0271221 A1 | 10/2009 | Aridi et al. | |
| 2010/0036680 A1* | 2/2010 | Familant | G06Q 10/10 705/3 |
| 2010/0117799 A1 | 5/2010 | Dormer et al. | |
| 2010/0131299 A1 | 5/2010 | Hasan et al. | |
| 2010/0169123 A1 | 7/2010 | Maus et al. | |
| 2010/0185496 A1 | 7/2010 | Hahn et al. | |
| 2010/0324936 A1 | 12/2010 | Vishnubhatla et al. | |
| 2012/0066017 A1* | 3/2012 | Siegel | G06Q 10/063112 705/7.14 |
| 2012/0215578 A1* | 8/2012 | Swierz, III | G06Q 50/205 705/7.14 |
| 2013/0238349 A1 | 9/2013 | Sethumadhavan et al. | |
| 2014/0136559 A1* | 5/2014 | Kottaram | G06Q 50/22 707/756 |
| 2014/0257842 A1* | 9/2014 | Heinze | G06F 17/30011 705/2 |
| 2014/0278832 A1* | 9/2014 | Glavina | G06F 19/366 705/7.42 |
| 2016/0048643 A1* | 2/2016 | Woods | G16H 10/60 705/3 |

\* cited by examiner

SYSTEMS AND METHODS FOR SORTING FINDINGS TO MEDICAL CODERS

CROSS REFERENCE TO RELATED APPLICATION

This non-provisional application claims the benefit of and is a continuation-in-part of U.S. provisional application No. 61/883,967 filed on Sep. 27, 2013, of same title, which application is incorporated herein in its entirety by this reference.

BACKGROUND

The present invention relates generally to systems and methods for sorting findings to one or more medical coders. The present systems and methods enable maximization of coder time and ability in order to facilitate exploration of the findings, and/or exploit the findings to maximize one or more criteria.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is that human intervention is required to perform medical coding. Medical coding (also known as clinical coding, diagnostic coding or health care coding) is the analysis of clinical statements and records to assign standardized codes using a classification system. The resulting coded information is integral to health information management, including statistical analysis by governments and healthcare organizations, research, epidemiological studies, health resource allocation, billing and education, among other uses.

The issues with medical coding arise from the fact that it is a highly manual process, and results in erroneous or improper coding. In order to combat this, multiple quality assurance steps typically need to be employed, which adds to the cost and burden of medical coding. Likewise it is very difficult to generate proper analytics regarding coders or coding due to the often iterative quality assurance steps.

It is therefore apparent that an urgent need exists for a medical coder sorter capable of assigning findings to a medical coder based upon coder abilities and quantifiable objectives. Such systems and methods enable more efficient medical coding, and further enable the generation of reports regarding coding.

SUMMARY

To achieve the foregoing and in accordance with the present invention, systems and methods for a medical coder sorter capable of assigning findings to a medical coder are provided. In particular, systems and methods for a medical coder sorter is provided which can dynamically provide findings to a coder based upon coder abilities and quantifiable objectives.

In some embodiments, the systems and methods receiving information about a user (coder), including identification, a role, and historical activity. Next the systems and methods may make a determination whether to run in exploration or exploitation modes. Exploration is used to explore the scope of the findings and also identify variables that impact a finding. Exploitation is designed to maximize a goal (such as throughput or profitability).

Lastly a finding is selected and provided to the user. The selection is based upon computing internal parameters when in exploration, or based upon optimizing for criteria when in exploitation. Computing the internal parameters may include selecting a finding randomly and analyzing the result, or may include providing the user a finding for which an assessment has already been performed. In contrast, the criteria that may be optimized for includes at least one of energy, value, predictive measure, and higher level rules. The higher level rules are configurable. The optimization determines what the user is good at based upon the criteria, and matches the user to a finding that requires what the user is good at.

The systems and methods may also be able to make a competency determination for the user, and cut them off from performing additional coding analysis if they are found incompetent. Competency may be determined by comparing at least one of time worked, findings assessed, and accuracy measures to a threshold, or via manual selection.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

Further note that, for the purposes of this disclosure, the term "finding", "opportunity" or "work" may be utilized interchangeably in order to signify work which is assigned to coders for annotation with medical codes. This work includes providing medical records to the coder for which they can identify the medical findings and extrapolate codes for them.

Figure 1:
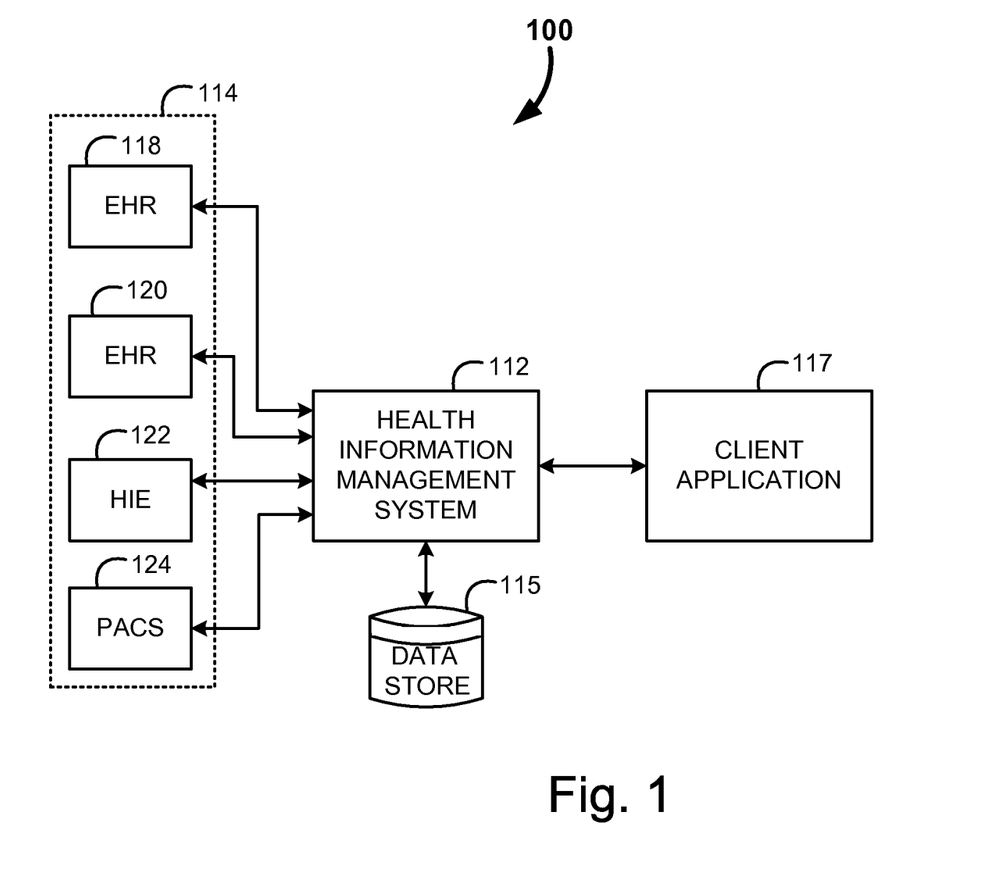
FIG. 1 shows a medical system, in accordance with an embodiment.

Referring now to FIG. 1, a medical system 100 is shown, in accordance with some embodiments. The system 100 is shown to include medical information sources 114, a health information management system 112, and medical information consumers/client applications (also referred to herein as "output" or "medical output") 117. The medical sources 114 are shown to include but not limited to an electronic health record (EHR) 118, EHR 120, health information exchange (HIE) 122, and a picture archiving and communication system (PACS) 124.

"Medical information", as used herein, may refer to any health-related information, including but not limited to patient medical records, patient entered information, care team entered information, healthcare device generated information, and billing information.

The sources 114 generally provides various medical information to the health information management system 112. For example, the EHRs 118 and 120 each may provide information such as medical records and billing, the HIE 122 may provide information such as medical records, and the PACS 124 may provide information such as diagnostic imaging and reports.

The medical information consumers/client applications 117, which may be made of a host of entities or individuals, such as patients, clinics, medical institutions, health organization, and any other medical-related party, use information that is provided by the health information management system 112. For example, user-customized processed medical information is provided by the health information management system 112 to a number of client applications 117. In this case, the health information management system 112 generates user-customized processed medical information to a plurality of users, with at least a portion of the user-customize processed medical information being provided to each of the users based on the relevancy of the portion being provided of each user's specific function or role and each user's associated security privileges.

In some embodiments, the health information management system may merely be a repository of health records and information. In alternate embodiments, the health information management system 112 may have sophisticated capabilities which enable it to index, map, and consolidate medical information, received from the sources 114, and also potentially enabling the tagging of this information, and reconciliation of the tagged information. In some methods and embodiments, information that is extracted from images is tagged to enhance recall of search queries. Indexing, at least in part, processes document and converts them into formats that allows for quick searching across a large collection of documents.

In some embodiments, the information in the health information management system 112 is encrypted and secure to ensure privacy of sensitive medical information.

It is understood that the sources 114 of FIG. 1 includes merely some examples of the sources that communicate with the health information management system 112 and that other sources, known to those in the field, are contemplated. Similarly, the output 117 may be used by those or entities not discussed herein but that are contemplated and within the scope and spirit of the invention.

Figure 2:
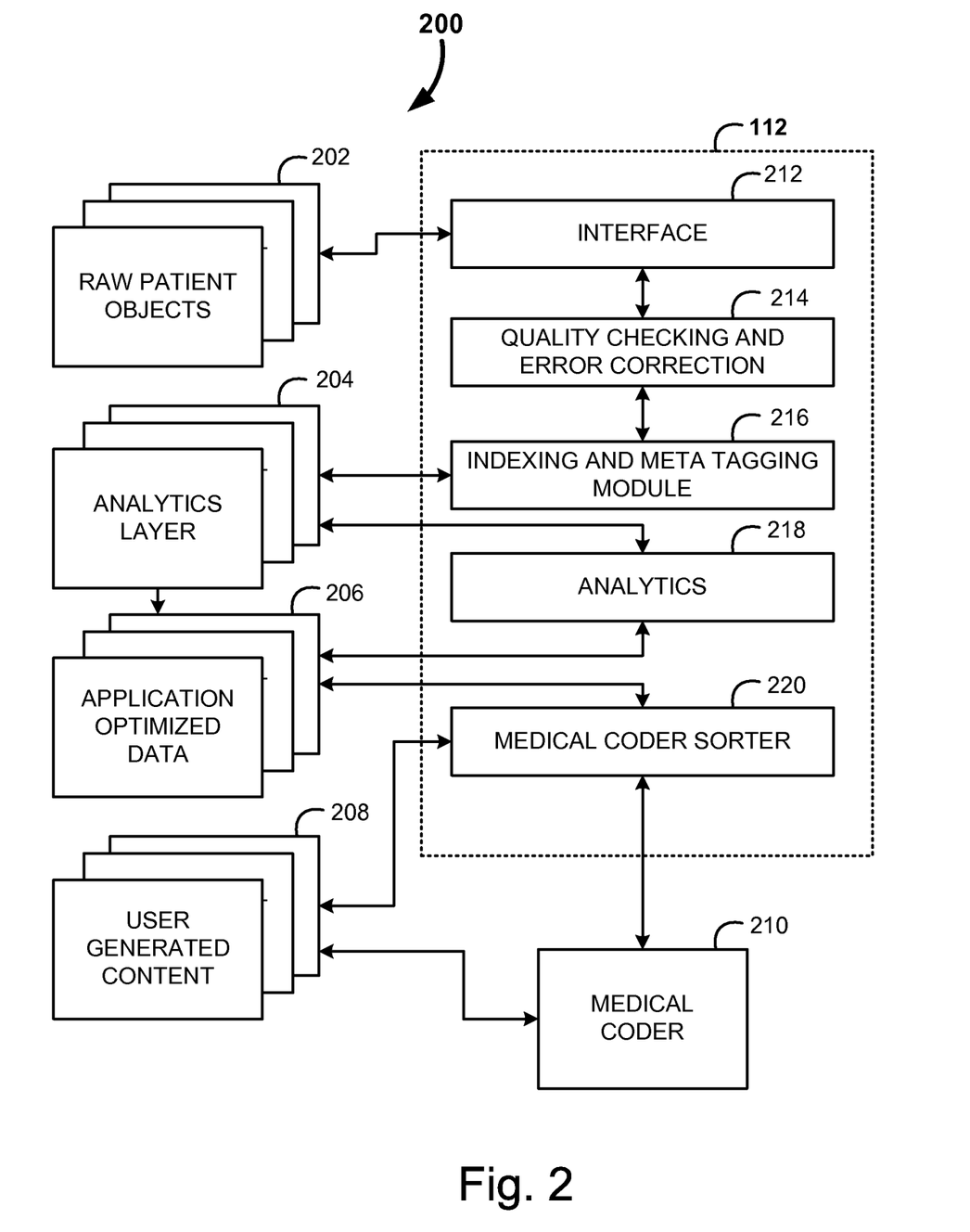
FIG. 2 shows further details of the system within a data architecture, including the medical coder sorter, in accordance with an embodiment.

Turning to FIG. 2, a more detailed illustration for the health information management system 112 is provided. In this example diagram, the health information management system 112 is interacting with multiple levels of data storage, shown generally at 200. The storage level begins with raw patient objects 202 which are received from the plurality of sources 114.

The health information management system 112 includes an interface 212 which can collect these objects. These objects 202 may be collected in various forms, such as but not limited to text, html, CCD, CCR, HL7, image and any other type or format information. The interface 212 then provides to the information to a quality checking and error corrector 214, in some embodiments.

The quality checking and error corrector 214 may simply delete duplicate errors and redundant patient medical records, such as, multiple records for the same individual appearing as though the records are for different individuals or multiple data elements that are recorded similarly but slightly differently in the different sources. The quality checking and error corrector 214 may also perform other basic and known error correction processes. Alternatively, more advanced quality checking and error corrector 214 systems may check the quality of medical information provided by various sources 114 by the patients, structured data, and unstructured data, in a Wiki-like mannered setting whereby the users can help maintain and improve the quality of information displayed.

In some embodiments, an indexing and Meta tagging module 216 may utilize a processor to processing the data, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others. The processed data may then be provided to the second level of the data storage architecture, the analytics layer 204. In some embodiments, the analytics layer 204 may be transient.

An analytics 218 module may take information from the analytics layer 204 and perform certain tasks on the information, which may include query, search, presentation, and quality checking. The output of the analytics 218 may be stored within the third layer of the data architecture, which is known as the application optimized data 206.

In some embodiments the medical coder sorter 220 accesses data that has been optimized for it, and determines whether to provide a finding to the medical coder 210. The medical coder 210 may code the finding and provide that data into a fourth level of the data architecture, which includes all user generated content 208. In some embodiments, the medical coder sorter 220 also generates reports about coding and coders which likewise may be stored in the user generated content 208 layer.

Figure 3:
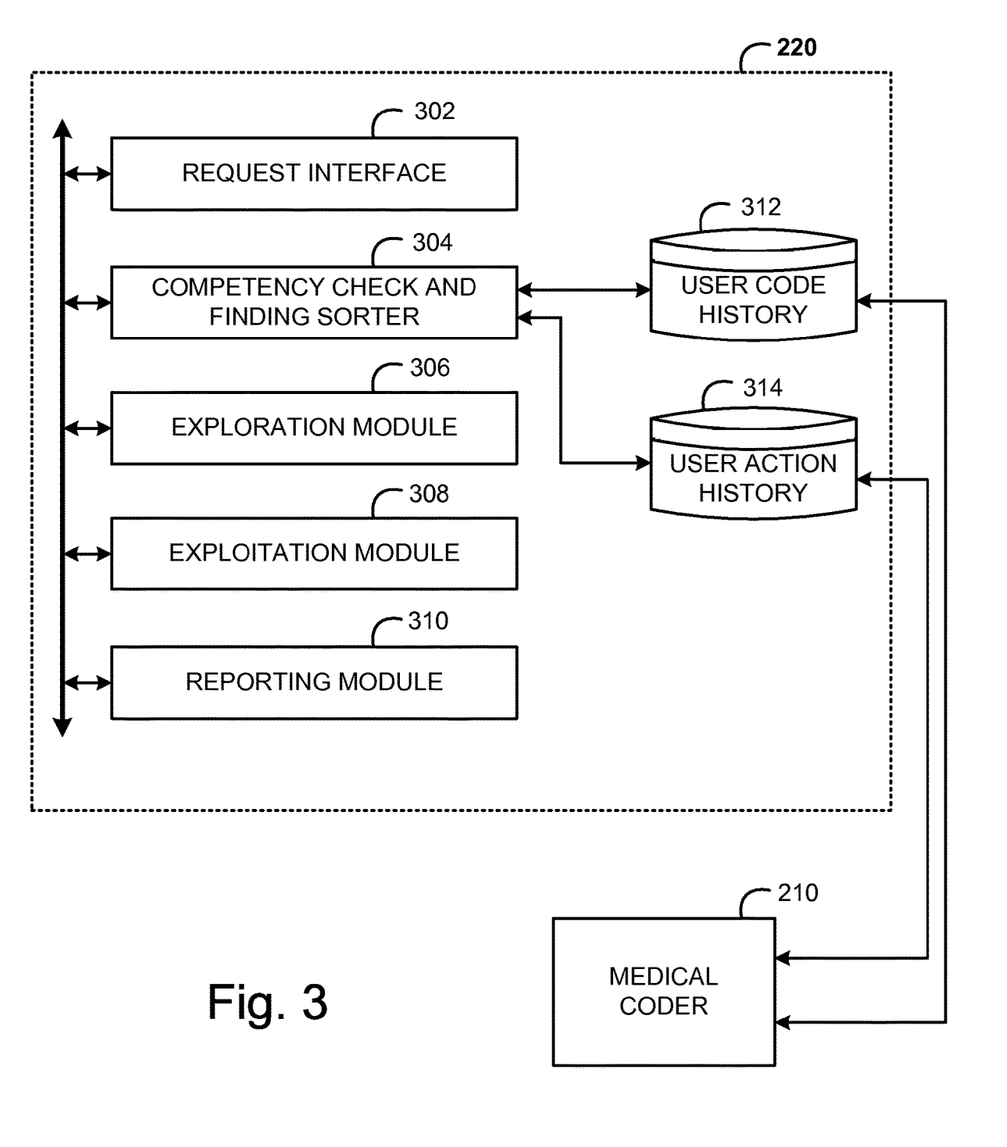
FIG. 3 shows an exemplary embodiment of the medical coder sorter, in accordance with an embodiment.

Turning to FIG. 3, a more detailed illustration of the medical coder sorter 220 is provided. Here it can be seen that the medical coder sorter 220 include a request interface 302, a competency check and finding sorter module 304, an exploration module 306, and exploitation module 308 and a reporting module 310. These subsystems may be logically of physically coupled within the medical coder sorter 220. The medical coder sorter 220 may also include, or have access to, databases of user coding history and recent user action history, 312 and 314 respectively. These databases are compiled using information generated from monitoring the medical coder 210.

The medical coder sorter 220 may work on a response model in which the client (often the clinical coder) requests a piece of work (also referred to as a finding or opportunity). The request includes the user's identification and the user's role. The medical coder sorter 220 accesses the coding history for the user. This coding history may be stored as a series of records in a database (as illustrated), or may be maintained as a state for the user. Further previous actions of the user may also be collected. Previous actions include any action taken by the user regarding the finding that was given previously by the medical coder sorter 220.

In response to the request the medical coder sorter 220 determines if it is in an exploratory or exploitation mode. Exploration refers the ability to explore the scope of the findings to estimate the parameters that control the coding. One way to undergo exploration would be to send a coder findings for which the coding is known. The coder's responses may then be compared to the known values for the finding in order to measure parameters that influence the coder or coding. Alternately, randomized findings may be selected to generate metrics regarding the user.

Exploitation refers to the ability to select a finding for the user which optimizes one, or a combination of, factors. These factors may include, but are not limited to, energy, expected value per unit of time, predictive measure of coder's performance and higher level rules. Higher level rules may include user configurable rules such as recoding of suspect items, etc. Energy, as used herein, is defined as the probability of acceptance of the code multiplied by the prevalence of the code. The predictive measure of the coder's performance may include historical measures of how often the user's output is in disagreement with that of another coder.

The medical coder sorter 220 thus determines, based upon a percentage of time whether exploration or exploitation is desired. Additionally, a determination may be made as to whether the user is competent to continue coding. If the user is competent, the medical coder sorter 220 selects a finding based upon the exploration or exploitation criteria, and provides the finding, along with any evidence for it, to the user.

The medical coder sorter 220 may also generate metrics based upon user activity, which is used to populate the historical databases, and to generate reports.

Figure 4:
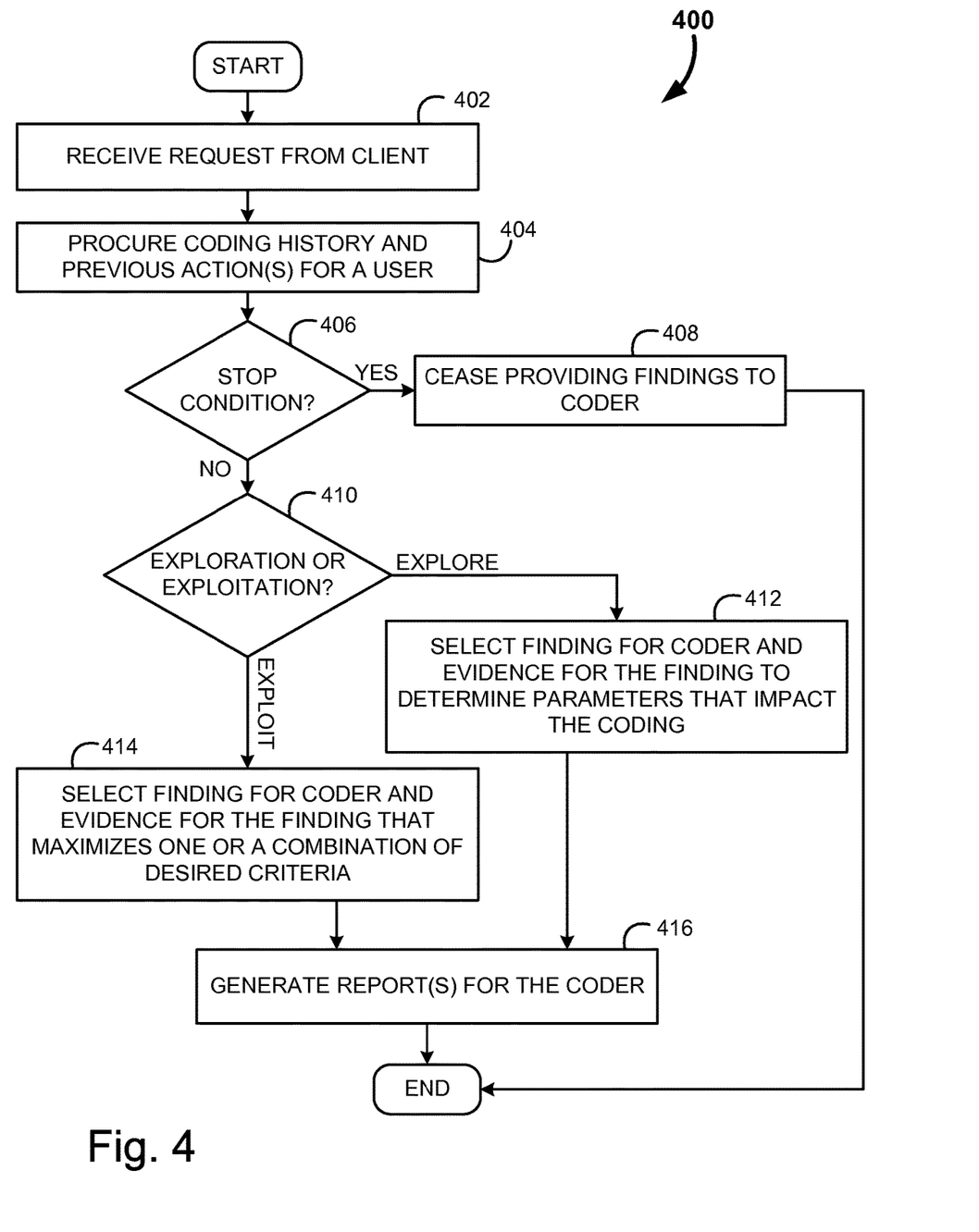
FIGS. 4-9 show a flow charts for the process of sorting findings to medical coders, in accordance with an embodiment of the invention.
Figure 5:
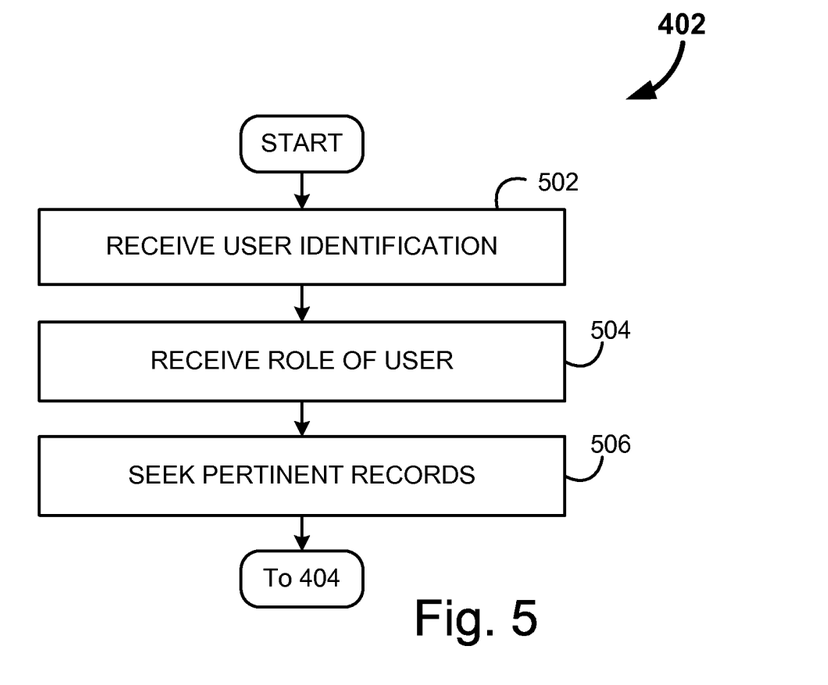

FIG. 4 provides an example process flow diagram for the sorting of findings, shown generally at 400. The first step in the process is to receive a request from a client (at 402). As previously mentioned, this client may include a coder or other user, or may include a medical information system, administrator, insurance group or medical care provider. A more detailed process flow diagram for this request is shown at FIG. 5. The user identification is received (at 502) for the request. The user's role is also received (at 504). Lastly, the pertinent records a sought (at 506) for the user.

Figure 6:
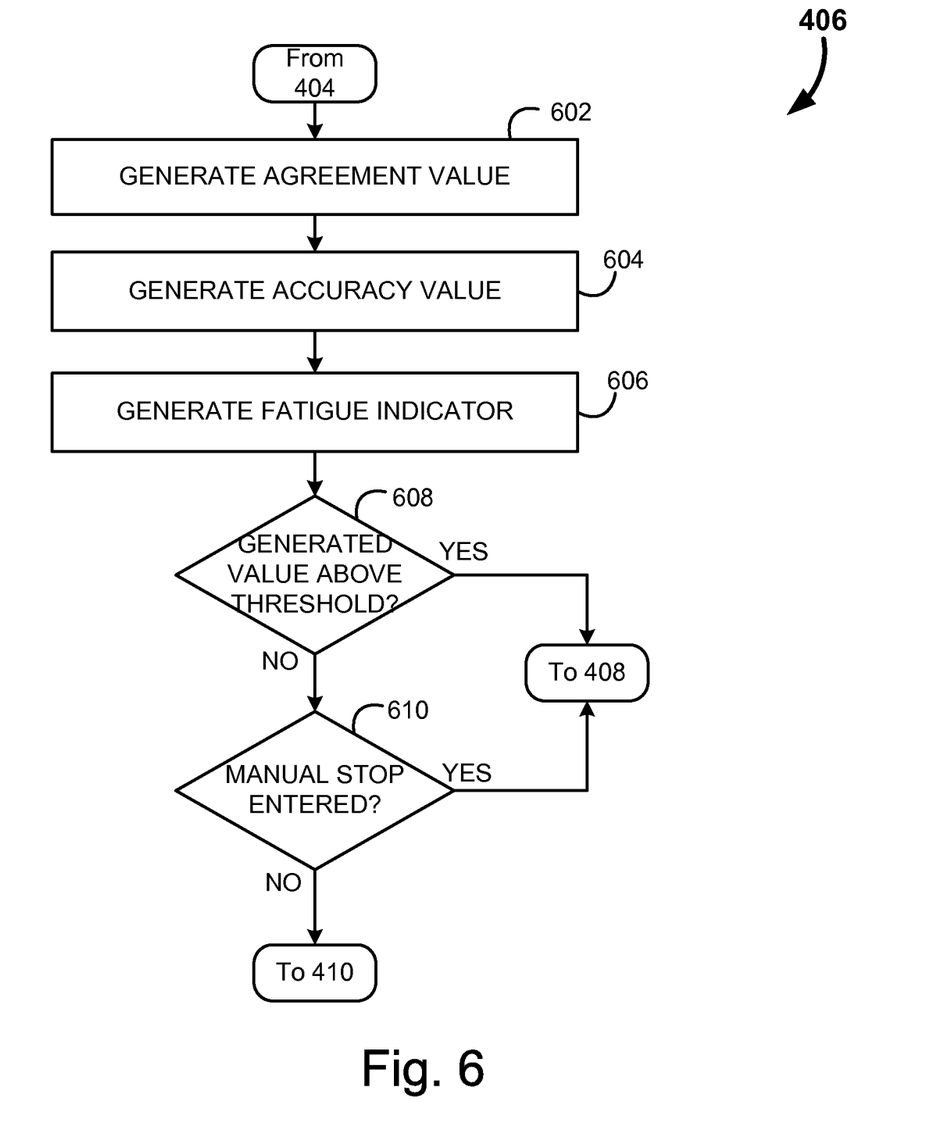

Returning to FIG. 4, the pertinent records include coding history for the user and previous actions of the user, which are procured (at 404). Next, a determination is made whether a stop signal is present which may indicate that the user is not competent to continue coding (at 406). FIG. 6 provides a more detailed process flow diagram for this decision making process. The system may generate an agreement value for the user (at 602). Agreement value may consist of how often the user's coding results are in agreement with the coding results of other users. Likewise, an accuracy value for the user may be generated (at 604). Accuracy values indicate how often the user properly identifies a finding and assigns the accurate code to the finding. Further, a fatigue indicator is generated for the user (at 606). Fatigue may manifest in a number of ways, including the duration of time the user has been continuously coding, rapid increase in error rates, longer time spent on findings before assigning codes, or trivial error rates.

If any of these values are above a desired threshold (at 608), then the user may be determined to be incompetent for further coding. Likewise, there may be a manual interrupt (at 610) which allows a manager, administrator or other party to discontinue findings being sent to a coder.

Figure 7:
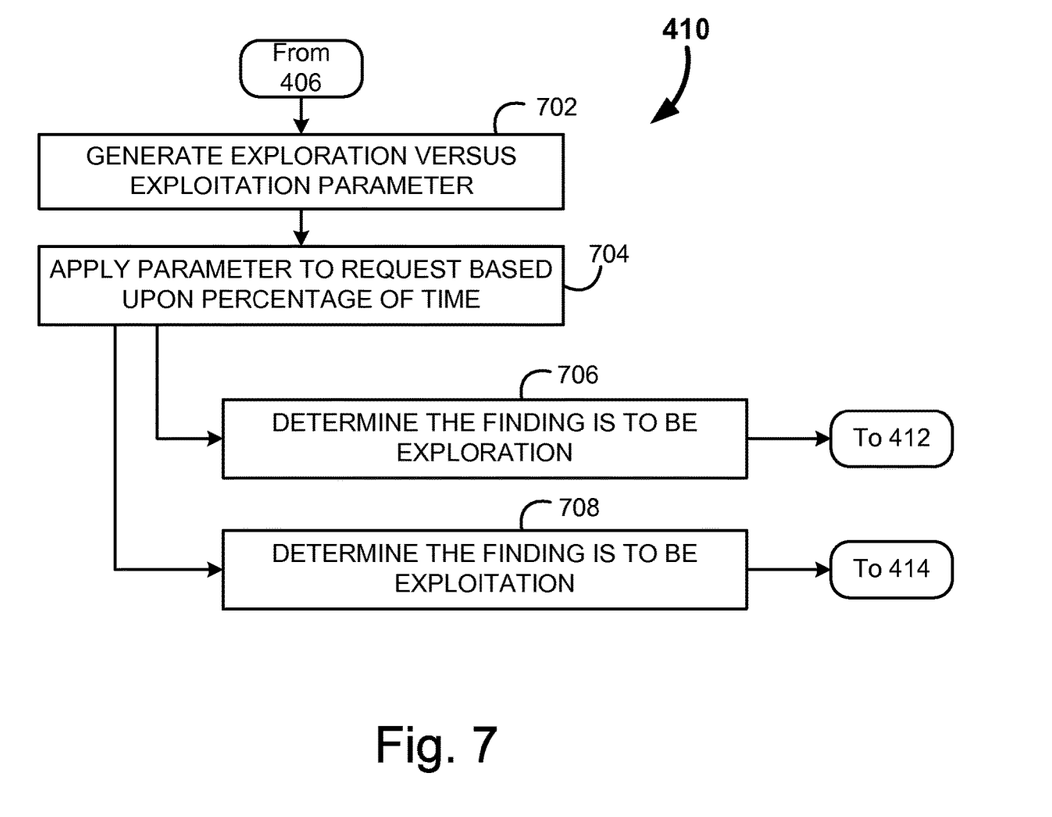

Returning to FIG. 4, if a stop condition is met the process ceases to provide findings to the coder (at 408) and the process ends. Otherwise, if the user is still allowed to receive findings, the process may determine if an exploration finding or an exploitation finding is to be provided (at 410). FIG. 7 provides a more detailed process flow diagram for this decision making process. Initially a parameter of exploration versus exploitation is generated (at 702). This parameter may be a static ratio, or may be a dynamic ratio, such as a decaying value. In these cases the decay rate can be configurable. The parameter is applied to the request based upon the time the request is received and according to the percentage of time the parameter indicates the system should operate in an exploration versus exploitation mode (at 704). This allows the finding to be determined as exploration or exploitation (at 706 and 708 respectively).

Figure 8:
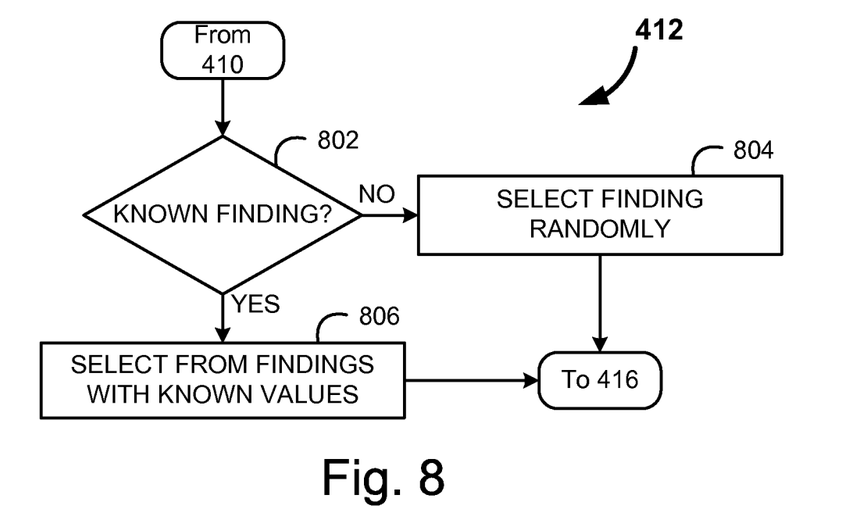

Returning to FIG. 4, the next steps are to select a finding for the coder, and provide the evidence for that finding, based upon exploration goals (at 412) or exploitation goals (at 414). FIG. 8 provides a more detailed process flow diagram for the selection when in exploratory mode. Here a decision is made whether a finding with a known code is to be selected (at 802). If so, then a finding is selected from those that the result is already known in order to compare coder responses (at 806). These comparisons may be utilized to determine parameters that impact coder responses. If no findings are known, or it is not desirable to use a known finding, a random finding could also be selected (at 804). The user's responses to randomized findings may be compared to the expected results distributions and statistically significant deviations may be identified. In this manner, findings may be selected which expand the understanding of the findings, and the parameters that impact their coding.

Figure 9:
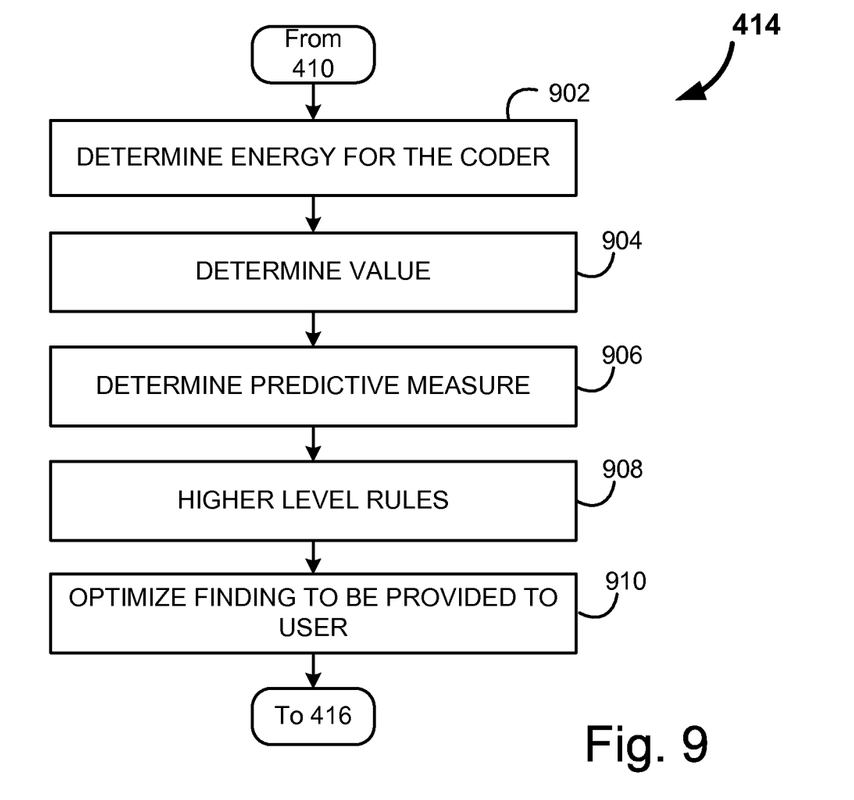

In contrast, FIG. 9 provides the process for selecting a finding when under exploitation mode. Here the energy for the coder is determined based upon historical actions (at 902). Likewise, the amount of money a particular user is likely to generate per a period of time is determined (at 904). For example, a coder may be much faster than other coders, and may therefore clear a larger sum in a period of time.

Alternatively a coder may identify larger valued codes that are often overlooked by other coders.

Next, the predictive ability for the user is determined (at 906). The predictive measure may include how often the user's work product is recoded in historical records during quality assurance. Additionally, higher level rules can be quantified (at 908), such as identifying findings that are suspect and flagging them for reassessment. Higher level rules may be created, read, updated and deleted by a user, administrator or other entity to ensure peak performance of the sorting.

One or more of these criteria may then be optimized for in order to match a finding to the user which meets the goal (at 910). For example, if quality of codings has been at issue, the system may maximize the recoding of suspect records (higher level rule) with users who have high predictive accuracy. Thus, if the user were to have high accuracy historically, they would receive a finding that is suspect. However, if the user has less than optimal accuracy, but historically generates codes for findings very quickly, suspect records may be held back and rather simpler finding may be provided to the user. In this manner the system may determine what the user is good at, and present findings which most closely match the user's strengths in order to maximize coding efficiency.

Returning to FIG. 4, after the finding has been provided to the user one or more reports may likewise be generated (at 416). These reports may include the energy, value, and predictive accuracy for a user. It may also generate behavior profiles for the coders. Reports may also include analytics into what was coded, rate of findings being assessed, and the like.

Figure 10A:
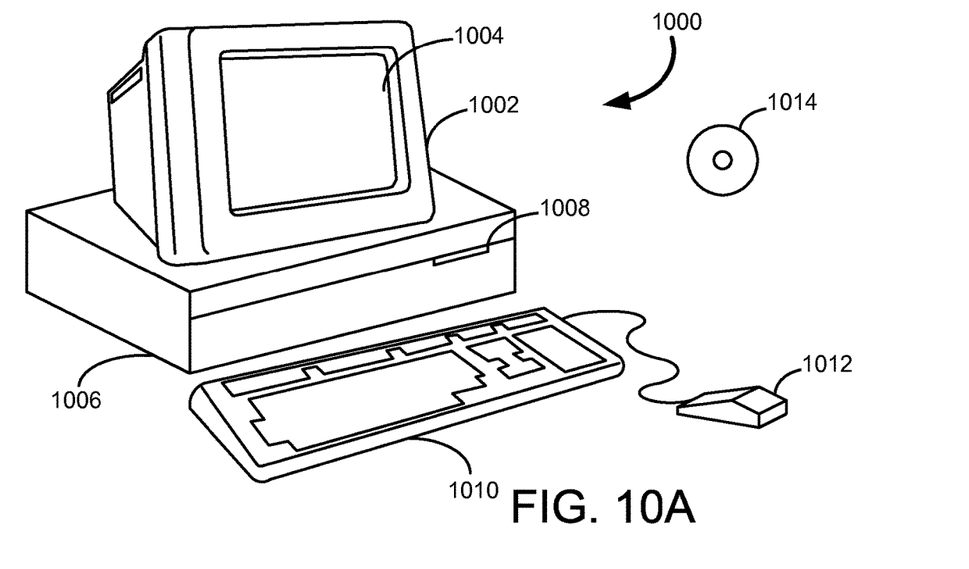
FIGS. 10A and 10B are example illustrations of a computer system capable of embodying the current invention.

FIGS. 10A and 10B illustrate a Computer System 1000, which is suitable for implementing embodiments of the present invention. FIG. 10A shows one possible physical form of the Computer System 1000. Of course, the Computer System 1000 may have many physical forms ranging from a printed circuit board, an integrated circuit, and a small handheld device up to a huge super computer. Computer system 1000 may include a Monitor 1002, a Display 1004, a Housing 1006, a Disk Drive 1008, a Keyboard 1010, and a Mouse 1012. Disk 1014 is a computer-readable medium used to transfer data to and from Computer System 1000.

Figure 10B:
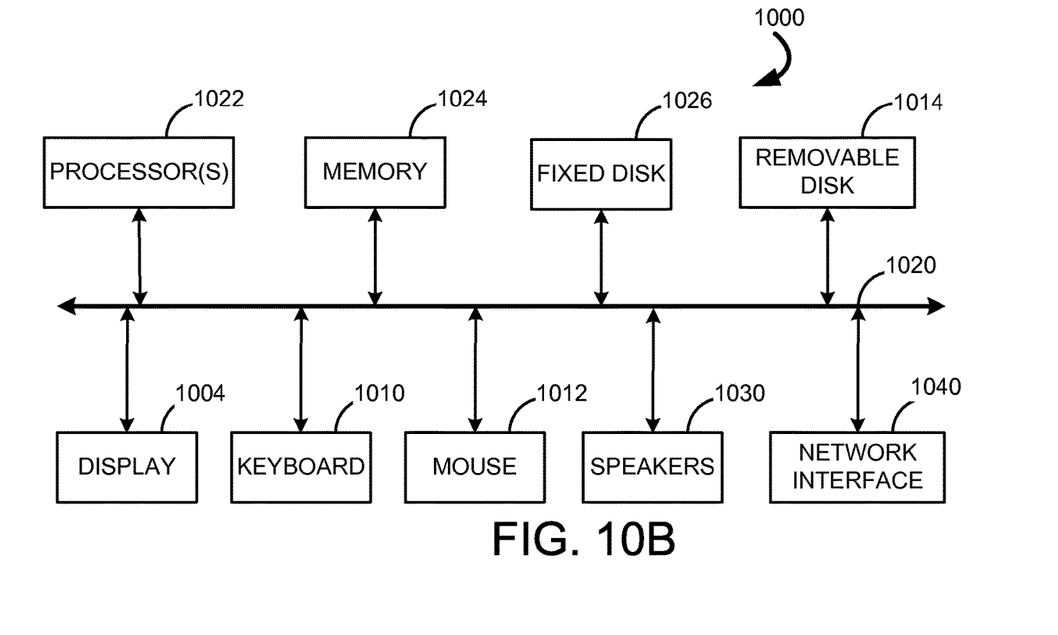

FIG. 10B is an example of a block diagram for Computer System 1000. Attached to System Bus 1020 are a wide variety of subsystems. Processor(s) 1022 (also referred to as central processing units, or CPUs) are coupled to storage devices, including Memory 1024. Memory 1024 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1026 may also be coupled bi-directionally to the Processor 1022; it provides additional data storage capacity and may also include any of the computer-readable media described below. Fixed Disk 1026 may be used to store programs, data, and the like and is typically a secondary storage medium (such as a hard disk) that is slower than primary storage. It will be appreciated that the information retained within Fixed Disk 1026 may, in appropriate cases, be incorporated in standard fashion as virtual memory in Memory 1024. Removable Disk 1014 may take the form of any of the computer-readable media described below.

Processor 1022 is also coupled to a variety of input/output devices, such as Display 1004, Keyboard 1010, Mouse 1012 and Speakers 1030. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1022 optionally may be coupled to another computer or telecommunications network using Network Interface 1040. With such a Network Interface 1040, it is contemplated that the Processor 1022 might receive information from the network, or might output information to the network in the course of performing the above-described finding sorting. Furthermore, method embodiments of the present invention may execute solely upon Processor 1022 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. In a health information management system, a computerized method for sorting findings to users, wherein all steps are performed by a processor, comprising:

receiving information about a user, including identification, a role, and historical activity;

receiving a plurality of findings in a plurality of medical records, wherein each finding is assigned a monetary reimbursement value and a label as either suspect or not;

calculating a predictive measure of the user's coding by identifying a rate the coder's coding is recoded during a quality assurance process using the user's historical activity;

calculating the user's speed of coding using the user's historical activity;

calculating the user's value per time responsive to the speed of coding in the user's historical activity and value of the codes found by the user;

selecting one finding from the plurality of findings determined by when the predictive measure is above an accuracy threshold selecting a finding with the suspect label, and when the user's speed is above a speed threshold and the predictive measure is below the accuracy threshold selecting a finding without the suspect label;

providing the selected finding, along with evidence associated with the selected finding, to the user via the interface of the health information management system, wherein the evidence associated with the finding is a subset of processed medical information; and restricting access to the user to the health information management system when a fatigue indicator for the user is identified, wherein the fatigue indicator includes at least one of duration of continuous coding by the user, and acceleration of an increase in error rates by the user, increasing time spent per coding by the user.

2. The method of claim 1, further comprising determining if the user is competent.

3. The method of claim 2, wherein competency is determined by comparing at least one of time worked, findings assessed, and accuracy measures to a threshold.

4. The method of claim 2, wherein competency is determined by manual selection.

5. The method of claim 1, wherein the historical activity includes user's past coding history.

6. The method of claim 1, further comprising comparing the codes already known for the finding to an assessment made by the user.

7. A system for sorting findings to users comprising:
a database configured to receive information about a user including identification, a role, and historical activity, and receive a plurality of findings in a plurality of medical records, wherein each finding is assigned a monetary reimbursement value and a label as either suspect or not;

a processor for calculating:
a predictive measure of the user's coding by identifying a rate the coder's coding is recoded during a quality assurance process using the user's historical activity;
the user's speed of coding using the user's historical activity;
calculating the user's value per time responsive to the speed of coding in the user's historical activity and value of the codes found by the user;

a sorting computer system for selecting one finding from the plurality of findings determined by when the predictive measure is above an accuracy threshold selecting a finding with the suspect label, when the user's speed is above a speed threshold and the predictive measure is below the accuracy threshold selecting a finding without the suspect label providing the selected finding, along with evidence associated with the selected finding, to the user, wherein the evidence associated with the finding is a subset of processed medical information; and an access controller for restricting access to the user to the health information management system when a fatigue indicator for the user is identified, wherein the fatigue indicator includes at least one of duration of continuous coding by the user, and acceleration of an increase in error rates by the user, increasing time spent per coding by the user.

8. The system of claim 7, further comprising a circuit configured to determine if the user is competent.

9. The system of claim 8, wherein the circuit compares at least one of time worked, findings assessed, and accuracy measures to a threshold.

10. The system of claim 8, wherein the circuit includes a manual stop function.

11. The system of claim 7, wherein the historical activity includes user's past coding history.

12. The system of claim 7, wherein the processor is further configured to-compare the codes already known for the exploratory finding to an assessment made by the user.

* * * * *